US007731703B2

(12) United States Patent
Matsuda et al.

(10) Patent No.: US 7,731,703 B2
(45) Date of Patent: Jun. 8, 2010

(54) MEDICAL BAG WITH A SUPPORT MEMBER AND GRASPING HOLES

(75) Inventors: Shinya Matsuda, Fukuroi (JP); Shoso Mukai, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 77 days.

(21) Appl. No.: 11/756,439

(22) Filed: May 31, 2007

(65) Prior Publication Data

US 2007/0282296 A1 Dec. 6, 2007

(30) Foreign Application Priority Data

May 31, 2006 (JP) ............................ 2006-150834

(51) Int. Cl.
*A61B 19/00* (2006.01)

(52) U.S. Cl. ....................... 604/403; 604/408; 604/409; 604/410; 604/411; 384/107; 384/109; 206/219; 206/484

(58) Field of Classification Search ................. 604/403, 604/408–411
See application file for complete search history.

(56) References Cited

U.S. PATENT DOCUMENTS

| | | | | |
|---|---|---|---|---|
| 2,878,849 | A | 3/1959 | Lingenfelter et al. | |
| 3,251,390 | A | 5/1966 | Evans | |
| 3,331,421 | A | 7/1967 | Lambert | |
| 4,356,954 | A * | 11/1982 | Mojonnier | 383/204 |
| 4,650,452 | A | 3/1987 | Jensen | |
| 4,838,872 | A * | 6/1989 | Sherlock | 604/319 |
| 4,869,725 | A | 9/1989 | Schneider et al. | |
| 4,903,718 | A * | 2/1990 | Sullivan | 134/184 |
| 5,728,087 | A * | 3/1998 | Niedospial, Jr. | 604/408 |
| 6,290,392 | B1 * | 9/2001 | Sandor | 383/33 |

FOREIGN PATENT DOCUMENTS

JP 06-098922 4/1994

OTHER PUBLICATIONS

Extended European Search Report dated Sep. 13, 2007 regarding Application No. 07010498.9-1257.

* cited by examiner

*Primary Examiner*—Tatyana Zalukaeva
*Assistant Examiner*—Ilya Y Treyger

(57) ABSTRACT

A medical bag formed of a flexible material includes a front bag part and a rear bag part joined together to form a bag body. A closable liquid inlet port is provided in an upper part of the bag body. The medical bag further includes a deformable elongated member provided in the vicinity of the liquid inlet port on at least one of the front and rear bag parts. The elongated member is deformable so as to retain the liquid inlet port in an open configuration when the elongated member is in a deformed state.

18 Claims, 6 Drawing Sheets

MEDICAL BAG WITH A SUPPORT MEMBER AND GRASPING HOLES

FIELD OF THE INVENTION

The present invention generally relates to a medical bag which is used for supplying a medical liquid such as a drip or nutrients to inside a patient's body, the bag is characterized by a retainable, deformable member and a pair of grasping holes for one hand operation of the bag.

BACKGROUND OF THE INVENTION

It is conventional practice to supply medical liquids such as medicinal products and nutrients by keeping the tip end part of a catheter inside a patient's body, for example. In cases such as these, a medical bag is connected to the rear end part of the catheter, and the medical liquid housed inside the medical bag is supplied to inside the patient's body via the catheter (see Japanese Patent Application H6-98922, for example). This medical bag (infusion container) is configured by a container main body made of thermoplastic resin, a contents filling part which is integrally provided with the container main body, a contents dispensing part adjacent to the contents filling part and integrally provided with the container main body and a sheet-shaped part in which a suspension aperture is formed. Then, the contents filling part is used to fill the medical bag with medical liquid, with the contents dispensing part being used to dispense medical liquid from inside the medical bag to the outside, and the contents filling part and the contents dispensing part are respectively configured by roughly cylindrical aperture parts.

However, with a conventional medical bag as described above, the contents filling part and the contents dispensing part are configured by a fairly rigid material which does not lose its shape, and the respective aperture parts are held open. Consequently, when this medical bag is packaged after production, there is a problem in that it ends up being bulky. Furthermore, the roughly cylindrical contents filling part and contents dispensing part must be moulded, and therefore there are problems in that the shape of the medical bag becomes complex and the production costs are increased.

For example in U.S. Pat. No. 4,869,725, use is also made of medical bags equipped with a zip-type medical liquid inlet port which is opened and closed with a detachable linear groove part and projection. However, with medical bags equipped with this zip-type medical liquid inlet port, when the medical bag is filled with medical liquid it is necessary for the user to handle the container which contains the medical liquid and to transfer the medical liquid in the container to the medical bag with one hand, while holding the medical liquid inlet port open with the other hand, and therefore problems arise in that the operation to fill the medical bag with medical liquid is troublesome.

SUMMARY OF THE INVENTION

In one aspect of the present invention, a medical bag formed of a flexible material generally comprises a front bag part and a rear bag part joined together to form a bag body. A closable liquid inlet port is provided in an upper part of the bag body. The medical bag comprises a retainable deformable elongated member provided in the vicinity of the liquid inlet port on at least one of the front and rear bag parts. Two grasping hole parts at opposite ends of the member are along the axis of the retainable, deformable elongated member. When the user deforms the member, the member retains its deformed position to keep the liquid inlet port in an open position or close position.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
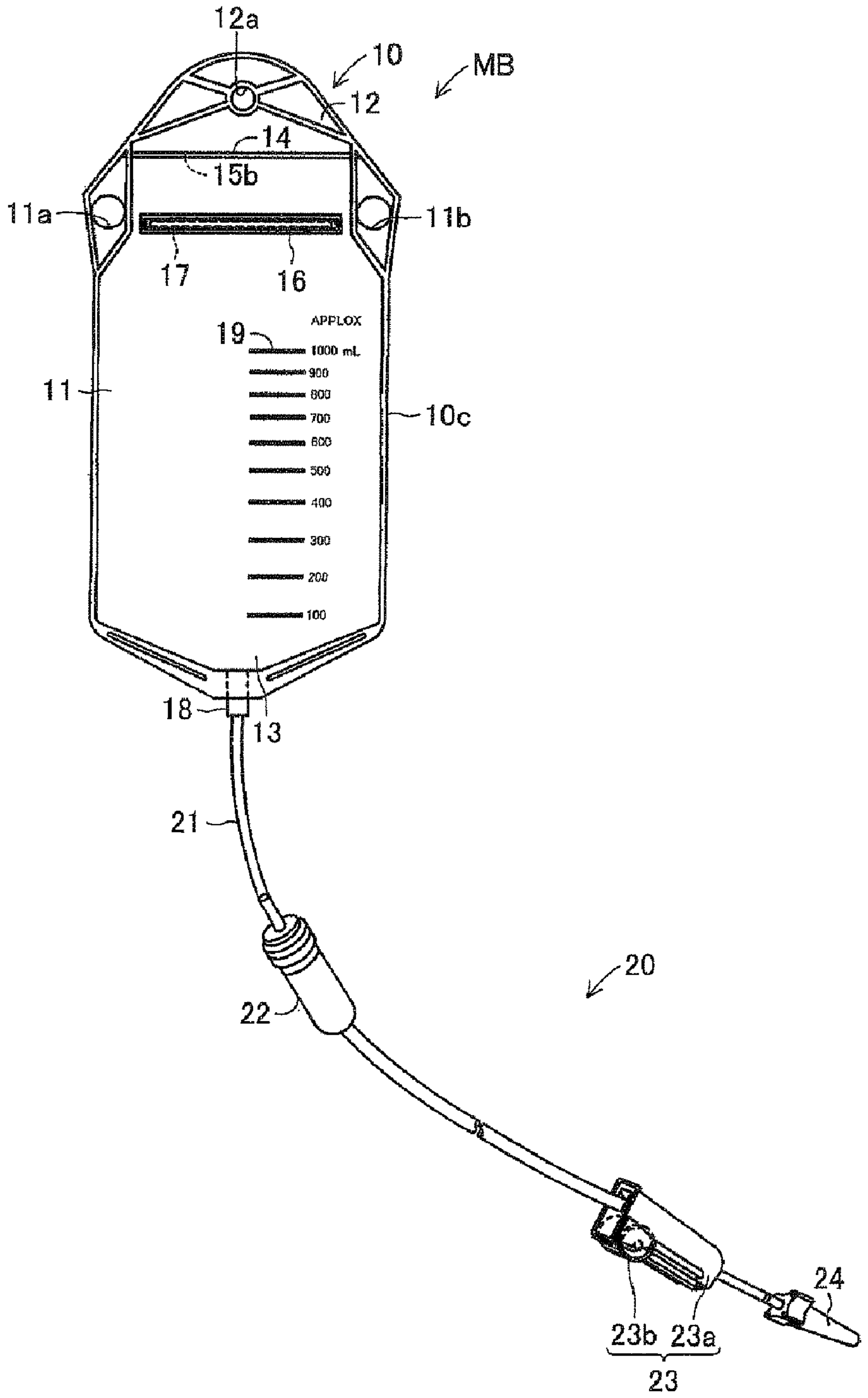
FIG. 1 is a front view showing the medical bag pertaining to one mode of implementation of the present invention.

A medical bag pertaining to a first mode of implementation of the present invention will be described in detail below using the figures. FIG. 1 shows the medical bag MB pertaining to this mode of implementation. This medical bag MB is used for supplying a medical liquid such as medicinal products or nutrients to inside a patient's body, and it is connected to a catheter (not shown in the figures, which remains in the patient's stomach or intestine etc., via the nose, throat or esophagus, and medical liquid ML (see FIG. 6) is supplied to inside the patient's body via the catheter. This medical bag MB is equipped with a bag main body 10 which acts as the bag member of the present invention and comprises a transparent soft film, and a medical liquid dispensing member 20 which is detachably attached to the bag main body 10.

Figure 2:
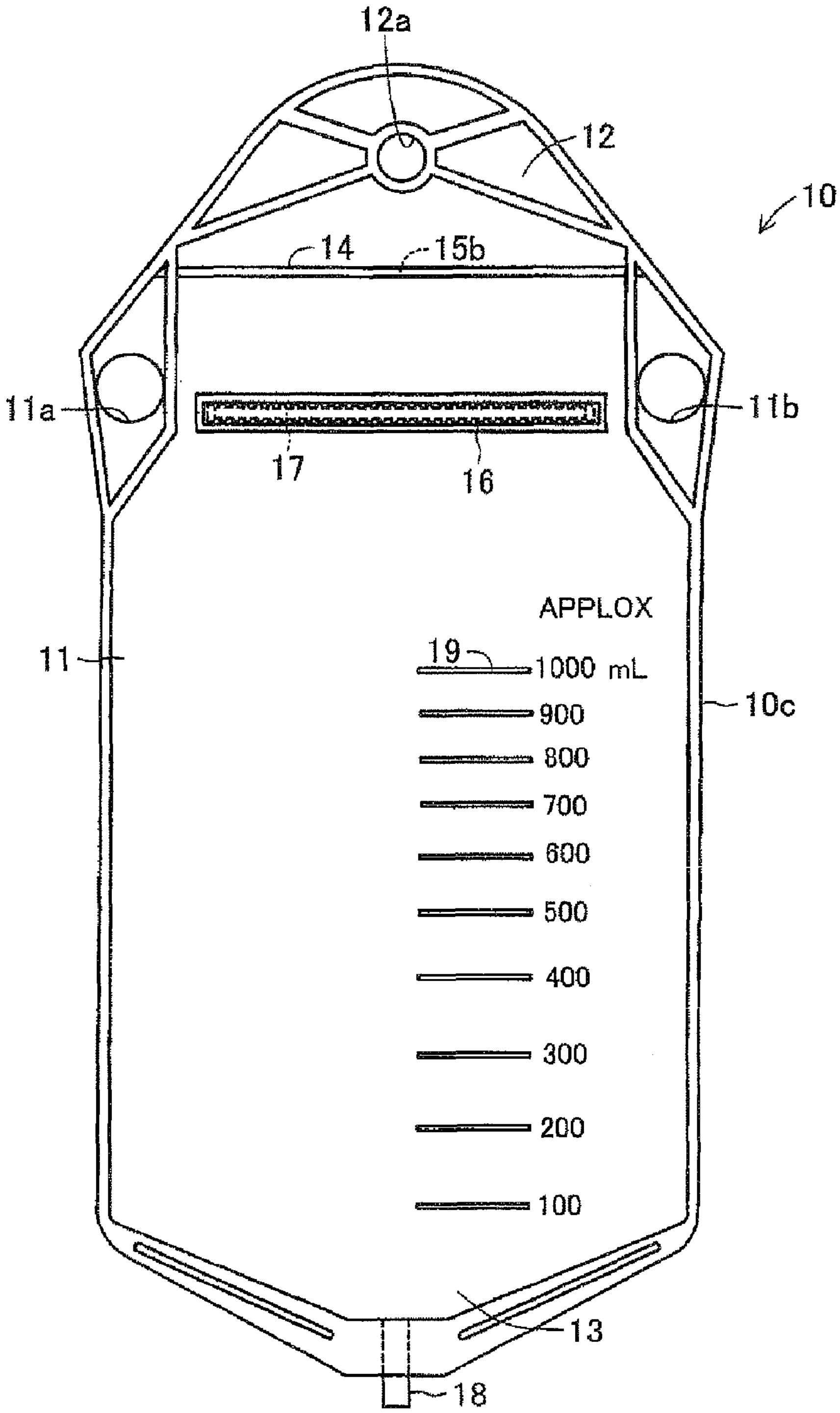
FIG. 2 is a front view showing the bag main body.

As shown in FIG. 2, the bag main body 10 is formed as a roughly hexagonal bag shape in which its central portion 11 forms an oblong box shape, and projecting portions 12, 13 which are roughly triangular in shape and project respectively upwards and downwards are formed on the top part and bottom part thereof. Then, a suspension hole part 12*a* is formed in the centre of the projecting portion 12 at the top of the bag main body 10, and grasping hole parts 11*a*, 11*b* to be respectively held by the fingers of the user are formed on both side portions of the top end part of the central portion 11 of the bag main body 10.

Figure 3:
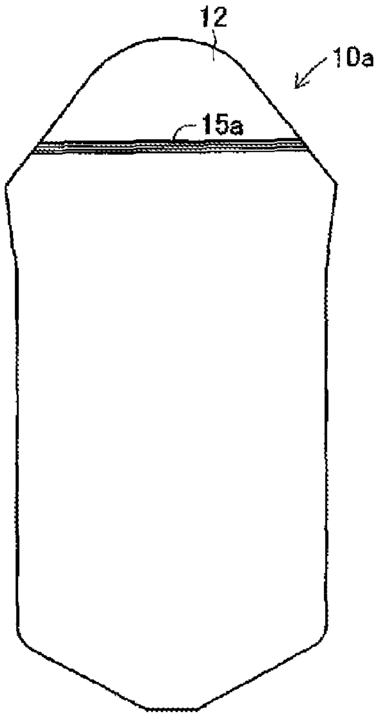
FIG. 3 is a front view showing the rear part of the bag main body.
Figure 4:
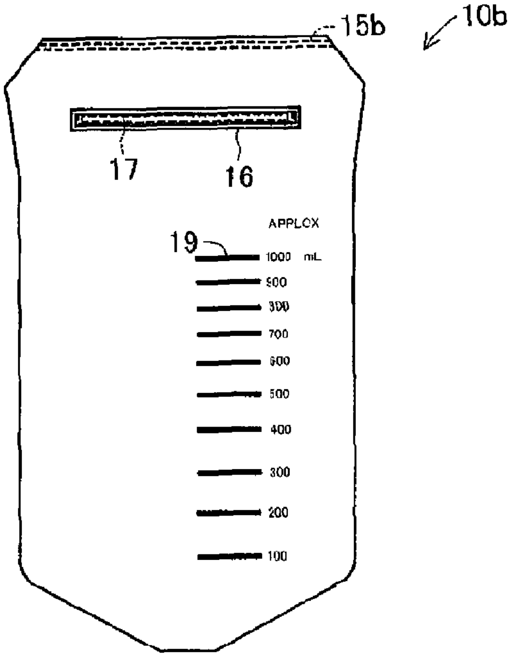
FIG. 4 is a front view showing the surface part of the bag main body.

Furthermore, the bag main body 10 is formed by the joining of the peripheral edge parts of the rear part 10*a* shown in FIG. 3 and the surface part 10*b* shown in FIG. 4 by means of heat sealing. In other words, the rear part 10*a* is configured by a film which, seen from the front, has virtually the same shape as the bag main body 10, and the surface part 10*b* is formed with a shape which lacks the portion on the upper side corresponding to the projecting portion 12 on the rear part 10*a*. Then, the surface part 10*b* is overlaid on the rear part 10*a*, and the rear part 10*a* and the surface part 10*b* are formed into the shape of a bag by means of the joining of the peripheral edge parts excluding the top end edge part of the surface part 10*b* using heat sealing, to form a linear joining part 10*c*.

Furthermore, a linear medical liquid inlet port 14 pertaining to the present invention is configured by a portion of the rear part 10*a* corresponding to the upper end edge part of the surface part 10*b* and an upper end edge part of the surface part 10*b*. Then, a linear engagement part 15*a* comprising a groove part and a projection which are vertically aligned and extend horizontally is formed on a portion of the inner surface (the surface corresponding to the surface part 10*b*) of the rear part 10*a* which corresponds to the upper end edge part area of the surface part 10*b*, and a linear part 15*b* to be engaged comprising a projection and a groove part, which are vertically aligned and extend horizontally is formed in the vicinity of the upper end edge part of the inner surface (the surface corresponding the rear part 10*a*) of the surface part 10*b*.

The groove part and the projection which said linear engagement part 15*a* and linear part 15*b* to be engaged are respectively equipped with and are able to engage with each other, and the bag main body 10 can be sealed shut by means of the engagement of said linear engagement part 15*a* and linear part 15*b* to be engaged, while the medical liquid inlet port 14 of the bag main body 10 is opened by means of the release of the engagement between the linear engagement part 15*a* and the linear part 15*b* to be engaged. Furthermore, an elongated sealing housing part 16, which extends parallel with the linear part 15*b* to be engaged is formed in a portion of the upper side portion of the surface part 10*b* in the area below the linear part 15*b* to be engaged, and a linear member 17 acting as the elongated member of the present invention, which, can be made of aluminium or a similar material is housed inside said sealing housing part 16. The linear member 17 retains its deformed position upon the application of a force, either pushing at the ends of the linear member 17 to cause the member 17 to form an arc, thus opening the bag. A pulling force can be applied to the linear member 17 to straighten or substantially close the bag opening. In both operations, the user inserts a finger in each grasping hole part 11*a*, 11*b* and applies a force. At FIG. 5, the bag is shown in an open position between 15*a* and 15*b*, after the user has applied a pushing force in the direction of the arrow at P. At FIG. 6, the bag is shown in a closed position at 15*b*, after the user has applied a pulling force in the direction of the arrow at P.

Figure 5:
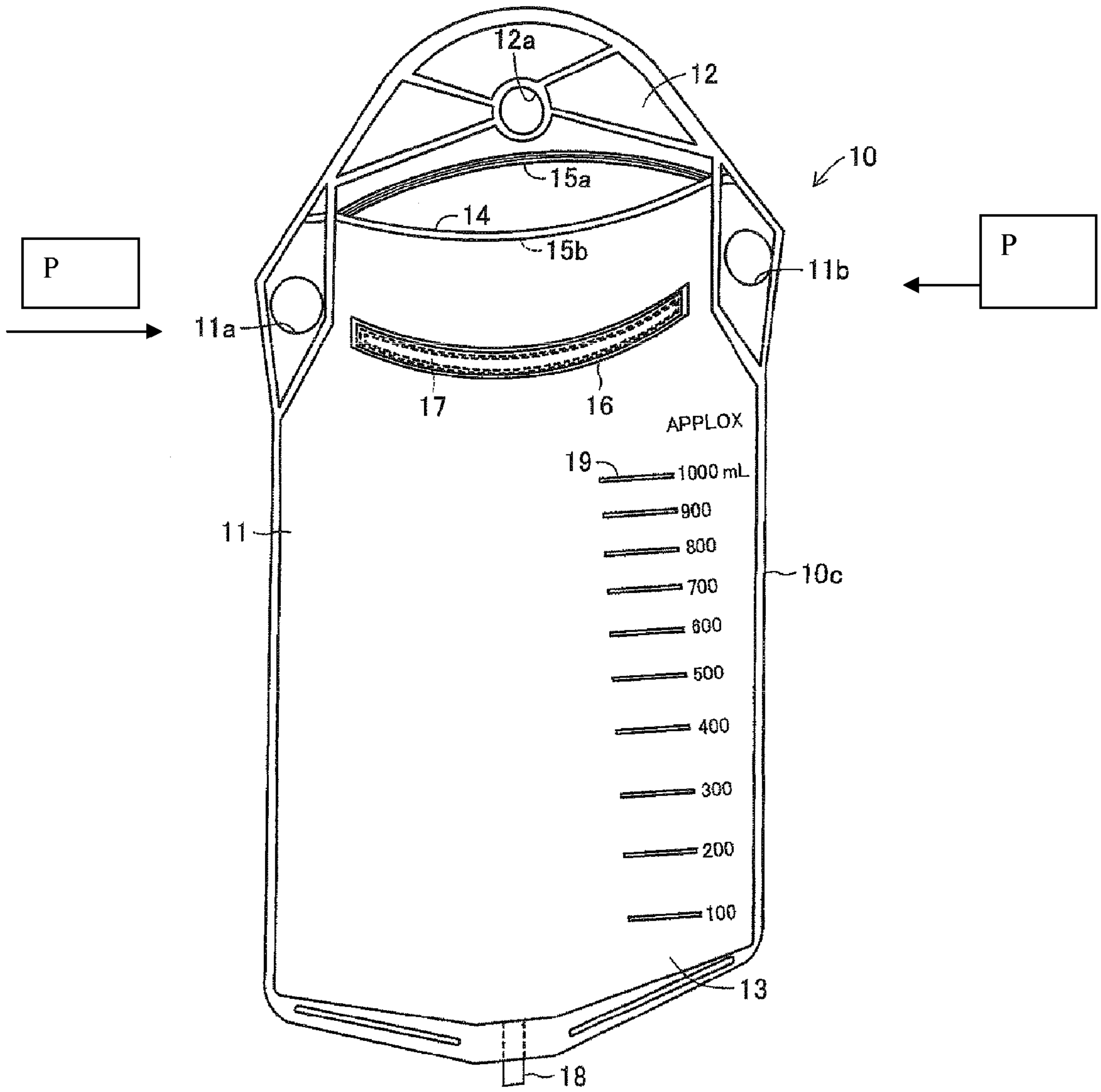
FIG. 5 is an oblique view showing the medical liquid inlet port of the bag main body in an open state.

Said linear member 17 is endowed with flexibility, and when the user bends it with his hands, it curves readily, and, as shown in FIG. 5, the linear member's curved state is retained after it is deformed. Accordingly, in the case where the medical liquid inlet port 14 is open, the medical liquid inlet port 14 can be held open by bending the linear member 17 into an arc shape, and the medical liquid inlet port 14 can be closed by extending the linear member 17 into a straight line. Furthermore, a cylindrical attachment part 18 for attaching the medical liquid dispensing member 20 is fixed to the lower end part of the projecting portion 13 of the bag main body 10.

Said attachment part 18 is configured by a soft material, and it is fixed to the lower part between the rear part 10*a* and the surface part 10*b* in a state in which the inside and the outside of the bag main body 10 are linked in communication. Furthermore, graduations 19 for showing the volume of medical liquid ML housed inside the bag main body 10 are printed on the surface of the bag main body 10 (the surface part 10*b*). Moreover, the bag main body 10 has a configuration in which the surface part 10*b* is overlaid on the rear part 10*a* in a state in which the attachment part 18 is arranged between the lower end parts of the rear part 10*a* and the surface part 10*b*, and the peripheral edge parts excluding the upper end edge part of the surface part 10*b* are joined by heat sealing, after which the suspension hole part 12*a* and the grasping hole parts 11*a*, 11*b* are formed. Furthermore, the components which configure said bag main body 10, are configured from polyvinyl chloride. The grasping hole parts 11*a*, 11*b* are formed through the medical bag near the linear member 17. The hole parts 11*a*, 11*b* are at opposite ends of the retainable, deformable elongated member 17, also called the linear member 17. The hole parts 11*a*, 11*b* are positioned along the same axis as the linear member 17. In operation the user inserts a finer through each of the grasping hole parts 11*a*, 11*b*. The user applies a compressive force to open the bag at FIG. 5, which deforms the linear member into an arc. The arc shape is retained until the user applies a force to pull the linear member 17 substantially closed. During use the user suspends the bag by keeping her fingers in the holes 11*a*, 11*b* and with the bag open, uses her other hand to pour liquid into the bag.

The medical liquid dispensing member 20 is configured by a tube 21, a flow-volume checking device 22 which is provided on the upstream side portion (the bag main body 10 side) of the tube 21, a flow-volume regulation device 23 which is provided on the downstream side portion of the tube 21, and a joining part 24 which is provided at the downstream end of the tube 21. The flow-volume checking device 22 is configured by a container-shaped roughly cylindrical body which has a diameter which is larger than that of the tube 21, and it is configured so that the medical liquid ML which flows inside the tube 21 from the upstream side to the downstream side becomes a liquid in drop form and drops down from the upper part to the lower part. Consequently, the flow volume of the medical liquid ML which flows inside the tube 21 can be checked by counting the number of falls for the time that drops are falling inside the flow-volume checking device 22.

Furthermore, the flow-volume regulation device 23 is configured by a trough-shaped main body portion 23*a* into which the tube 21 is inserted and a roller part 23*b* which is able to move inside the main body portion 23*a*. The roller part 23*b* is configured so that it can move along a guide part which is formed on the inside surface of the main body portion 23*a* in a state in which the gap with the bottom surface of the main body portion 23*a* can be varied. Consequently, the flow volume of the medical liquid ML which flows inside the tube 21 can be varied by changing the area of the hole part of the tube 21, by varying the position of the roller part 23*b* with respect to the main body portion 23*a*.

Furthermore, the joining part 24 can be joined to the catheter, and medical liquid ML which is sent from the tube 21 is supplied to inside the patient's body from the nasal cavity, for example, via the catheter. Moreover, the flow-volume regulation device 23 may be attached to a portion of the tube 21 between the flow-volume checking device 22 and the attachment part 18. In this case, the flow-volume of the medical liquid ML is regulated by setting the tube 21 or the tube and the flow-volume checking device 22 with a nutrition-supply pump (not shown in the figures).

With this configuration, in the case where the medical liquid ML is supplied to inside the patient's body using the medical bag MB, the engagement between the linear engagement part 15*a* and the linear part 15*b* to be engaged of the bag main body 10 is first of all released to open the medical liquid inlet port 14. Then, the linear member 17 is bent into an arc shape, to assume a state in which the medical liquid inlet port 14 is open, as shown in FIG. 5. By virtue of this, the linear engagement part 15*a* and the linear part 15*b* to be engaged are bent in a direction so that they separate from each other, and the medical liquid inlet port 14 is held open. Next, the medical liquid inside the container in which the medical liquid ML is housed is introduced into the bag main body 10 from the medical liquid inlet port 14.

Figure 6:
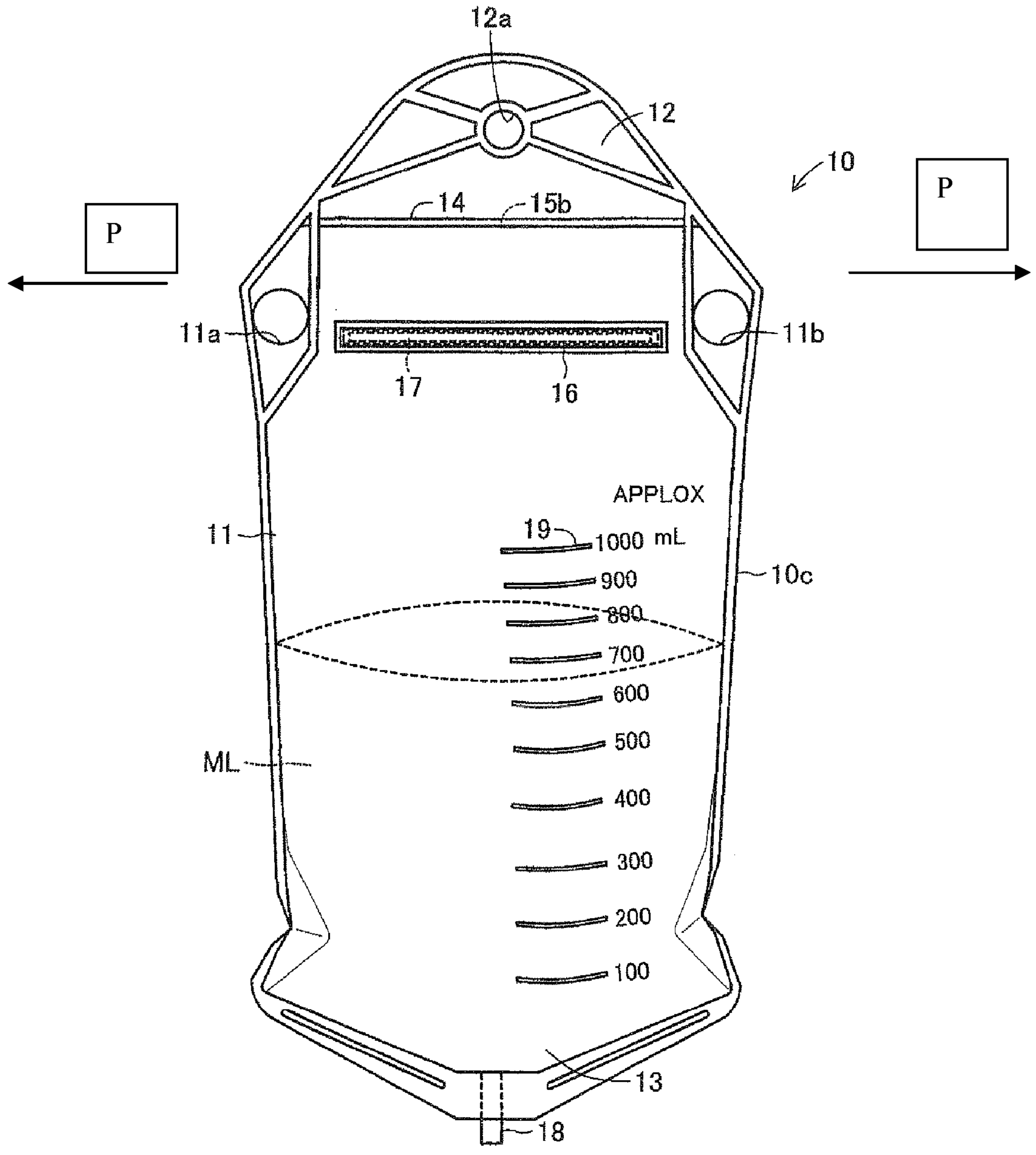
FIG. 6 is a front view showing the medical bag in a state in which it is filled with medical liquid.

Then, when the bag main body 10 is filled with a prescribed amount of the medical liquid ML, the linear engagement part 15*a* and the linear part 15*b* to be engaged are caused to engage, as shown by the state in FIG. 6. Next, said medical bag MB is suspended on the drip stand (not shown in the figures) by way of the suspension hole part 12*a*, and the joining part 24 is joined to the catheter. Then, the tip end part of the catheter is made to remain inside the patient's body and the medical liquid ML inside the bag main body 10 is supplied to inside the patient's body via the medical liquid dispensing member 20 and the catheter by means of the operation of flow-volume regulation device 23.

In this case it is possible to visually check the flow volume of the medical liquid ML which flows inside the tube 21 by means of the drops which fall inside the flow-volume checking device 22, and it is also possible to check the remaining volume of medical liquid ML inside the bag main body 10 using the gradations 19 on the surface of the bag main body 10. Then, when the medical liquid ML inside the bag main body 10 has run out and the medical liquid ML is to be replenished, the medical liquid inlet port 14 can be opened with the medical bag MB as it is suspended on the drip stand, and medical liquid ML can be introduced inside the bag main body 10.

In this way, with the medical bag MB pertaining to the present mode of implementation, the sealing housing part 16 is formed on the surface part 10*b* side in the vicinity of the medical liquid inlet port 14 which has a linear form, and the linear member 17 which is made of aluminium is provided inside said sealing housing member 16. Consequently, when the medical liquid inlet port 14 is opened and the medical liquid ML is introduced from the medical liquid inlet port 14, the linear member 17 deforms and it is possible for the medical liquid inlet port 14 to be held open. Consequently, there is no need for such operations as holding the medical liquid inlet port 14 with the hands and opening it, and the operation to fill the bag main body 10 with medical liquid ML is simplified.

Furthermore, the bag main body 10 is configured by a soft, flexible material, and also the medical liquid inlet port 14 has a linear form, and therefore when the medical bag MB is packaged, it does not become bulky even if it is folded, and it is possible to package the medical bag MB in a compact manner. In addition, the linear member 17 is configured by aluminium, and also the opening and closing of the medical liquid inlet port 14 is achieved using the linear engagement part 15*a* and the linear part 15*b* to be engaged, which respectively comprise a groove part and a projection, and therefore the medical bag MB is easily produced and also inexpensive.

Furthermore, the suspension hole part 12*a* is provided on the upper end side portion of the bag main body 10, and therefore the medical liquid inlet port 14 can be opened and the bag main body 10 can be filled with medical liquid ML in a state in which the medical bag MB is suspended from the drip stand. Consequently, the operation to fill the bag main body 10 with medical liquid ML is further simplified. In addition, the tube 21 of the medical liquid dispensing member 20 is detachable from the attachment part 18 which is provided on the lower end part of the bag main body 10, and therefore the dispensing port for dispensing the medical liquid ML can be made small, and the medical bag MB can be formed in a compact manner.

Figure 7:
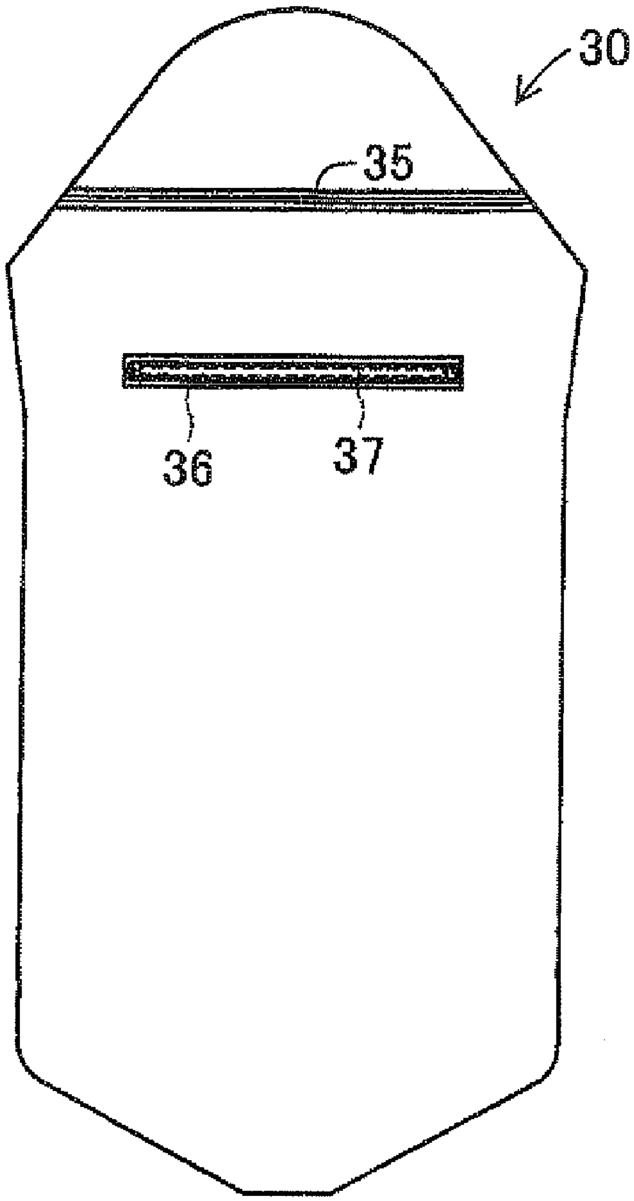
FIG. 7 is a front view showing the rear part which the medical bag is equipped with pertaining to another mode of implementation of the present invention.

Furthermore, FIG. 7 shows a rear part 30 which the medical bag is equipped with pertaining to another mode of implementation of the present invention. This rear part 30 is formed with the same shape as the abovementioned rear part 10*a* when viewed from the front, and a linear engagement part 35 having the same structure as the linear engagement part 15*a* is formed in the same place as the place where the linear engagement part 15*a* of the rear part 10*a* is provided. Then, an elongated sealing housing part 36 is formed on a portion of the rear part 30 below the linear engagement part 35, and a curved member 37 is housed inside said sealing housing part 36. Said curved member 37 is configured by an elongated board made of plastic, and it curves so that both side portions are positioned further forwards than the central side portion in FIG. 7. The configuration of the other components of said rear part 30 is the same as that of the rear part 10*a*. Furthermore, the configuration of the other components of the rear part 30 of the medical bag pertaining to this mode of implementation is the same as that of the medical bag MB described above.

This configuration is adopted, when the medical liquid inlet port is closed, the linear member 17 of the surface part 10*b* is caused to deform so that it runs along the curved member 37, and the linear engagement part 35 and the linear part 15*b* to be engaged are caused to engage. Furthermore, when the medical liquid inlet port is opened, the linear member 17 curves so that the centre side portion of the linear member 17 separates from the centre side portion of the curved member 37 in a state in which the engagement of the linear engagement part 35 and the linear part 15*b* to be engaged is released. The medical liquid inlet port is held wide open due to the curvature of said linear member 17 and curved member 37 in opposite directions. The other efficacious actions of the medical bag pertaining to this mode of implementation are the same as those of the medical bag described above.

Furthermore, the medical bag pertaining to the present invention is not limited to the modes of implementation described above and it can be implemented with appropriate modifications. For example, with the medical bag MB pertaining to the modes of implementation described above, the linear member 17 is provided only on the surface part 10*b*, but said linear member 17 may be provided on both the surface part 10*b* and the rear part 10*a*. By virtue of this, the medical liquid inlet port 14 can be reliably held open. Furthermore, with the mode of implementation described above, use is made of a linear member 17 which is made of aluminium, but a rod-shaped member or a plate-shaped member may be used instead of said linear member 17. The one or more elongated members may be attached to a surface part by means of an adhesive. Alternately, the elongated member could be inserted into an appropriately dimensioned pocket provided on said surface part.

Furthermore, aluminium alloy, copper, lead, steel or another deformable metal or other material can be used instead of aluminium as the material for configuring the linear member 17. In addition, it is possible to cover the surface of the aluminium or the like which configures the linear member 17, and the rod-shaped member or plate-shaped member, which configures the elongated member with a tube made of resin. Furthermore, it is also possible to provide a grasping piece which is held by the user's hand in the vicinity of the linear part 15*b* to be engaged on the bag main body 10 in order to simplify the opening and closing operation of the medical liquid inlet port 14 or the like. In addition, in the mode of implementation described above, the bag main body 10 is configured by the rear part 10*a* and the surface part 10*b* or the rear part 30 and the surface part 10*b*, but said bag main body 10 or the like may be configured by heat sealing the lower end part of a cylindrical member. Furthermore, it is also possible to implement the invention with appropriate modifications to other components which configure the medical bag.

As can be seen from the above description, at least the illustrated embodiment of the present invention provides a medical bag which is not bulky when packaged, entails a simple one hand operation to fill it with medical liquid, and can be produced without raised production costs.

In order to achieve the abovementioned advantages, the features of the configuration of the medical bag pertaining to at least one embodiment of the present invention lie in the fact that it is a medical bag in which an open/close-type medical liquid inlet port is linearly formed on an upper side portion of a bag member, the bag member is made of a soft, flexible material, and the medical bag is such that a retainable deformable elongated member which extends along the peripheral edge part near the medical liquid inlet port. The member is provided in the vicinity of the medical liquid inlet port on at least one of the surface part and the rear part of the bag member, and when the elongated member deforms and it is made to curve, the member holds the medical liquid inlet port open, and when the elongated member is deformed and the member becomes roughly linear, which causes the medical liquid inlet port to become roughly linear and be held closed. The opening is caused by pushing at the ends of the deformable member. The member retains its deformed state after the user stops pushing at the ends of the member. To return the member to its linear state, the user inserts her finger through each hold and pulls the member back to a substantial linear shape.

With the medical bag of at least one embodiment of the present invention configured in the manner described above, the medical liquid inlet port is configured by an open/close-type aperture part which is linear in shape or lengthwise at a top edge of the bag, and a deformable elongated member, which extends along the peripheral edge part of the medical bag is provided in the vicinity of said medical liquid inlet port. Consequently, when the medical liquid inlet port is opened and the medical liquid is introduced from the medical liquid inlet port, it is possible for the medical liquid inlet port to be held open by the retainable deformation of the elongated member. For example, in the case where the elongated member is provided on both the surface part and the rear part of the bag member, if the elongated member is deformed so that its shape becomes roughly annular, the peripheral edge part of the medical liquid inlet port is held open with a roughly annular shape due to the elongated member. The elongated member retains its shape when deformed, until the user applies a pulling force to cause the member to become linear, or a pushing force to cause the member to become arched. When arched, the user can use their other hand to pour a liquid into the open end of the medical bag. The one hand operation is simplified with a pair of holes at either end and along the same axis as the liner member. As described above, once the user inserts a finger in each hole to hold or suspend the bag, the user press the linear member to open the bag, or pull to straighten the liner member to close the bag using a single hand in both operations.

Furthermore, in the case where the elongated member is provided on only one of the surface part or the rear part of the bag member, the elongated member is deformed so that its shape becomes roughly semi-circular, and the peripheral edge part of the medical liquid inlet port is also held open with a roughly annular shape by means of the elongated member. In this case, the portion of the peripheral edge part of the medical liquid inlet port, which is not provided with an elongated member is also deformed with a curved shape symmetrical with the shape of the elongated member, and therefore the medical liquid inlet port is held open.

Consequently, the medical liquid inlet port is held open, and therefore there is no need, among other things, for the user to grasp the peripheral edge part of the medical liquid inlet port with the hand, thus the operation to fill the medical bag with medical liquid is simplified. Furthermore, the bag member is made from a soft, flexible material, and also the medical liquid inlet port is formed with a linear shape, and therefore when the medical bag is packaged, it is possible to package it in a compact manner without any bulkiness even if the bag is folded. A zip-type open/close aperture may be used for the medical liquid inlet port in this case, and by virtue of this the medical bag is simple to produce, and also inexpensive. Furthermore, an elongated member which is deformable and also which can retain its deformed shape and form an aperture for the medical liquid inlet port should be used as the elongated member, and it is possible to use a variety of shapes, such as an elongated plate shape or rod shape, or a narrow linear shape.

Furthermore, other features of the configuration of the medical bag pertaining to at least one embodiment of the present invention lie in the fact that the elongated member is configured by a linear member made of aluminium. By virtue of this, it is possible to make the medical liquid inlet port as a lightweight, rigid member. Furthermore, the elongated member may be configured by an inexpensive material, such as a resilient, yet pliable material such as polyvinyl chloride or PVC.

Furthermore, other features of the configuration of the medical bag pertaining to at least one embodiment of the present invention lie in the fact that the elongated member is provided on the surface part or the rear part of the bag member, and a flexible curved member is provided along the peripheral edge part of the medical liquid inlet port on the rear part or the surface part which is not provided with the elongated member in the vicinity of the medical liquid inlet port. By virtue of this, when the medical liquid inlet port is held open, the medical liquid inlet port can be held open reliably due to the fact that the elongated member deforms in a curving direction of the curved member and the opposite direction. Furthermore, an elongated board or the like made of plastic may be used as the curved member.

Furthermore, other features of the configuration of the medical bag pertaining to at least one embodiment of the present invention lie in the fact that a suspension hole part is provided on the upper end side portion of the bag member, and a medical liquid dispensing tube made of a soft material is joined to the lower end part of the bag member. By virtue of this, the dispensing port for dispensing the medical liquid may be made small, and therefore the medical bag can be formed in a compact manner. Furthermore, the suspension hole part is provided at the upper end side of the bag member, and therefore the medical liquid inlet port can open and the medical bag can be filled with medical liquid in a state in which the medical bag is suspended on a drip stand. Consequently, the operation to fill the medical bag with medical liquid is further simplified.

Having described the invention in detail, it will be apparent that modifications and variations are possible without departing from the scope of the invention defined in the appended claims.

When introducing elements of the present invention or the preferred embodiment(s) thereof, the articles “a”, “an”, “the” and “said” are intended to mean that there are one or more of the elements. The terms “comprising”, “including” and “having” are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical bag formed of a flexible material, comprising:
- a front bag part;
- a rear bag part, wherein the front bag part and the rear bag part are joined together to form a bag body;
- a closable liquid inlet port provided in an upper part of said bag body;
- a retainable deformable elongated member provided in the vicinity of said liquid inlet port on at least one of the front and rear bag parts, the retainable deformable elongated member defining an axis and being deformable by a hand of a user between a substantially straight position and an arched position; and
- two grasping hole parts at opposite ends of and along the axis of the retainable deformable elongated member, the retainable deformable elongated member configured such that when the hand of the user pushes the grasping hole parts axially toward each other, the retainable deformable elongated member is deformed into the arched position to keep the liquid inlet port in an open position, and such that when the hand of the user pulls the grasping hole parts axially away from each other, the retainable deformable elongated member is deformed into the substantially straightened position for closing the liquid inlet port.

2. The medical bag according to claim 1 wherein said linear member is made of metal.

3. The medical bag according to claim 2 wherein said metal is selected from the group consisting of aluminium, aluminium alloy, copper, lead, and steel.

4. The medical bag according to claim 1 wherein said closable liquid inlet port comprises elongated mutually cooperating tongue and groove sealing parts.

5. The medical bag according to claim 4 wherein one of said elongated mutually cooperating tongue and groove sealing parts forms an upper edge of one of said front and rear bag parts.

6. The medical bag according to claim 5 wherein said deformable elongated member is arranged on one of a front and rear bag parts different to the bag part having an upper edge forming said one of said elongated mutually cooperating tongue and groove sealing parts.

7. The medical bag according to claim 1 wherein said deformable elongated member is inserted into a pocket formed on one of said front and rear bag parts.

8. The medical bag according to claim 1 in which said deformable elongated member is adhered to one of said front and rear bag parts.

9. The medical bag according to claim 1 further comprising:
- a suspension hole defined in one of said front and rear bag parts; and
- a liquid dispensing tube joined to a lower part of said bag body.

10. A medical bag formed of a flexible material, comprising:
- a front bag part;
- a rear bag part, wherein the front bag part and the rear bag part are joined together along a right side edge, a bottom edge and a left side edge to form a bag body;
- a closable liquid inlet port provided along a top edge of the front bag part and rear bag part configured for selective opening and closing of the bag body, the closable liquid inlet port providing a first access to an interior of the bag body;
- an elongate sealing housing part provided in the vicinity of the liquid inlet port on one of the front and rear bag parts, the elongate sealing housing part providing a second access to the interior of the bag body, the elongate sealing housing part extending substantially parallel to the top edge and defining an axis, wherein the sealing housing part is configured to maintain an open configuration after an axial force is applied inwardly from both ends of the elongate sealing housing part and configured to maintain a closed configuration after an axial force is applied outwardly from both ends of the elongate sealing housing part; and
- a pair of grasping holes formed at opposite ends of and along the axis of the elongate sealing housing part, whereby the elongate sealing housing part is opened by axially moving the pair of grasping holes toward one another and the elongate sealing housing part is closed by axially moving the pair of grasping holes away from one another.

11. The medical bag according to claim 10, wherein the elongate sealing housing part includes an elongate hand deformable linear member capable of retaining its shape.

12. The medical bag according to claim 11, wherein the elongate hand deformable linear member is a length of at least one of aluminum, aluminium alloy, copper, lead, and steel.

13. The medical bag according to claim 10, wherein the closable liquid inlet port includes elongated mutually cooperating tongue and groove sealing parts.

14. The medical bag according to claim 13, wherein one of said elongated mutually cooperating tongue and groove sealing parts forms an upper edge of one of said front and rear bag parts.

15. The medical bag according to claim 11, wherein the deformable linear member is supported in one of a front and rear bag parts.

16. The medical bag according to claim 15, wherein the deformable linear member is inserted into a pocket formed on one of said front and rear bag parts.

17. The medical bag according to claim 15, wherein the deformable linear member is adhered to one of said front and rear bag parts.

18. The medical bag according to claim 10, further comprising:
- a suspension hole defined in one of said front and rear bag parts; and
- a liquid dispensing tube joined to a lower part of said bag body.

* * * * *